United States Patent [19]

Shook, Jr.

[11] 4,385,007
[45] May 24, 1983

[54] PREPARATION OF ZEROVALENT NICKEL COMPLEXES

[75] Inventor: Howard E. Shook, Jr., Orange, Tex.

[73] Assignee: E. I. Du Pont de Nemours and Company, Wilmington, Del.

[21] Appl. No.: 305,183

[22] Filed: Sep. 24, 1981

[51] Int. Cl.³ .................. C07C 120/02; C07C 121/26
[52] U.S. Cl. .......................... 260/465.8 R; 260/439 R
[58] Field of Search ..................... 260/465.8 R, 439 R

[56] References Cited

U.S. PATENT DOCUMENTS

| | | | |
|---|---|---|---|
| 3,496,218 | 2/1970 | Drinkard, Jr. | 260/465.8 R |
| 3,766,237 | 10/1973 | Chia et al. | 260/465.8 R X |
| 3,773,809 | 11/1973 | Walter | 260/465.8 R |
| 3,903,120 | 9/1975 | Shook, Jr. | 260/464.3 X |
| 4,082,811 | 4/1978 | Shook, Jr. | 260/465.8 R X |

*Primary Examiner*—Joseph Paul Brust

[57] ABSTRACT

Improved reaction rate for nickel powder in the preparation of zero-valent nickel organophosphite ligand complex catalysts using recycle catalyst and ligand.

3 Claims, No Drawings

PREPARATION OF ZEROVALENT NICKEL COMPLEXES

BACKGROUND OF THE INVENTION

1. Field of the Invention

The present process is directed to an improvement in the preparation of zero-valent nickel complexes which typically are used as catalyst for the production of dinitriles. More particularly, the present process is directed to the recovery of a zero-valent nickel catalyst promoted by an organoborane after the catalyst and promoter have been used in the production of adiponitrile by the hydrocyanation of 3- and/or 4-pentenenitriles.

2. Description of the Prior Art

U.S. Pat. No. 3,496,218 issued on Feb. 17, 1970 describes in general terms a process for the preparation of dinitriles especially adiponitrile by the hydrocyanation of non-conjugated, ethylenically unsaturated organic compounds, e.g., 3- and/or 4-pentenenitriles using certain nickel complexes as catalysts. The catalysts are promoted by organoborane compounds such as triphenylborane. A wide range of process conditions and relative amounts and types of reactants are disclosed.

A particularly useful form of zero-valent nickel catalyst is described in U.S. Pat. No. 3,766,237 issued on Oct. 16, 1973. The patentees disclose the use of an excess of the triarylphosphite ligand in the hydrocyanation along with the addition of certain ethers to improve the yield and increase the pounds of product which can be made per pound of catalyst consumed.

U.S. Pat. No. 3,903,120 issued on Sept. 2, 1975 discloses an improved process for the preparation of zero-valent nickel complexes with aromatic phosphorus compounds using a phosphorus halide as a catalyst to increase the reaction rate of elemental nickel. It is also disclosed that organic mononitriles and/or dinitriles increase the reaction rate when used as a solvent.

U.S. Pat. No. 3,773,809 issued on Nov. 20, 1973 discloses a process for separating organic phosphorus compounds and their metal complexes, e.g., the above-described catalysts, from organic nitriles by extracting the product fluid with a paraffin or cycloparaffin hydrocarbon solvent at 0°–100° C. The organic phosphorus compounds and their metal complexes are contained predominantly in the hydrocarbon phase and the organic mononitriles and dinitriles are predominantly contained in a separate phase.

SUMMARY OF THE INVENTION

In a process for the production of dinitriles by the addition of hydrogen cyanide to non-conjugated, unsaturated nitriles in the presence of a zero-valent nickel-organophosphorus ligand containing catalyst promoted with an arylborane wherein the product fluid from said addition is contacted with a paraffin or cycloparaffin at a temperature of at least 60° C. to form a primary light hydrocarbon extract phase containing catalyst values and a heavy dinitrile phase which phases are separated and wherein said catalyst is initially prepared by reacting elemental nickel with an organophosphorus compound, the improvement which comprises cooling said primary light extract phase sufficiently to form a secondary light phase and a secondary heavy phase, separating these phases, removing substantially all of said hydrocarbon from the secondary light phase, and returning the residue thus obtained from the secondary light phase to the initial catalyst preparation to react with said elemental nickel.

It is preferred to cool the light phase extract to less than about 45° C. and most preferably to a temperature in the range 20°–30° C.

DETAILED DESCRIPTION OF THE INVENTION

The present invention can be employed to improve catalyst usage in any hydrocyanation process which employs the zero-valent nickel catalyst as described herein where the product fluid is extracted with a paraffin or cycloparaffin. Of particular interest is the hydrocyanation of 3- and/or 4-pentenenitriles or mixtures thereof to produce adiponitrile (ADN) because ADN is an intermediate used in the production of hexamethylenediamine which in turn is used to produce polyhexamethyleneadipamide, a commercial polyamide useful in forming fibers, films and molded articles.

A preparation of zero-valent nickel [Ni(o)] catalyst to which the present invention is applied is found in U.S. Pat. No. 3,903,120 issued on Sept. 2, 1975 the disclosure of which is incorporated herein by this reference. Of particular interest is the preparation of a catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Excess ligand can be employed.

The promoters which are used with the above-described catalyst are tiarylboranes including those of the formula $BR_3$ wherein R is an aryl or substituted aryl group having 6 to 12 carbon atoms, e.g., phenyl, ortho-tolyl, para-tolyl, naphthyl, methoxyphenyl, biphenyl, chlorophenyl and bromophenyl. Triphenylborane (TPB) is preferred.

The method for conducting the hydrocyanation is not critical. It is preferred to employ a plurality of stages in series with the product from one stage being directed continuously to a subsequent stage and the hydrogen cyanide split between stages.

In order to separate dinitrile products from unreacted starting materials and catalyst which must be recycled for reasons of economy, the product fluid from the hydrocyanation is initially contacted with a paraffin or cycloparaffin according to the process described in U.S. Pat. No. 3,773,809 the disclosure of which is incorporated herein by this reference. In the case of the hydrocyanation of 3-pentenenitrile (3PN) and/or 4-pentenenitrile (4PN) to produce adiponitrile (ADN) using $NiL_4$ wherein L is a neutral ligand tri(mixed, meta- and para-) tolyl phosphite (TTP) as the catalyst and triphenylborane (TPB) as the promoter, a typical product fluid has the following average composition

| Component | Amount (% by weight) |
|---|---|
| $NiL_4$ | 0.4–0.8 (as Ni) |
| 3- and 4-PN | 10–20 |
| TTP | 20–40 |
| ADN + DN* | 40–60 |
| TPB | 0.2–0.8 |

*Dinitriles other than ADN such as 2-methyl-glutaronitrile and ethylsuccinonitrile.

The preferred extractant is cyclohexane employed at a volume ratio of 1–5, preferably 1–2, times the volume of product fluid. In order to achieve rapid phase separation and avoid emulsion formation while employing commercially acceptable amounts of extractant, it is necessary to conduct the extractant at a temperature of at least 55°-60° C. It is the light hydrocarbon phase which contains catalyst and which has been separated from the heavy dinitrile phase to which the present invention is applied. During hydrocyanation a portion of the nickel catalyst is deactivated to an extent which requires that the active nickel be replenished before the catalyst is reintroduced into the reaction. This replenishment is accomplished by introducing the recycled catalyst into the catalyst preparation at the step where elemental nickel is reacted with free ligand as particularly described in column 3, lines 10–45 of U.S. Pat. No. 3,903,120. However, this replenishment must be accomplished under unfavorable equilibrium conditions and therefore it is particularly important to maintain as rapid a reaction as possible for economic operation.

U.S. Pat. No. 3,903,120 discloses that mononitriles or dinitriles can be used as solvents to increase the rate of reaction between organophosphorus compounds and elemental nickel and since the light hydrocarbon phase obtained as described hereinabove contains mononitriles, dinitriles, ligand and zero-valent nickel, it would appear that these compounds could be directly recycled to the catalyst preparation after removal of the extractant to improve the efficiency of the process. However, it has been found that when such recycle is attempted, the rate of reaction of the elemental nickel decreases to an unacceptable level.

It has been discovered that the impaired reaction rate caused by catalyst recycle can be corrected by cooling the light hydrocarbon phase obtained as above until a second heavy phase is formed and then removing the heavier phase before removing the hydrocarbon. Usually the hydrocarbon phase must be cooled to less than about 45° C. and preferably to less than about 30° C. and in the range of 20°-30° C. to form a sufficient amount of a second heavy phase. The heavy phase resulting from this cooling which is not recycled does contain dinitriles e.g., ADN. It is surprising that removal of this heavier phase has a beneficial effect in view of U.S. Pat. No. 3,903,120 which teaches that dinitriles increase the rate of nickel reaction. One skilled in the art would predict that it is unnecessary and possibly harmful to remove any more dinitrile than is necessary to form a multiple phase mixture. Since the present process removes dinitrile and yet increases the rate of nickel reaction, it can be speculated that some other compound which is a poison to the reaction of nickel powder with free ligand is concurrently removed with the dinitrile. Clearly ADN is not the poison as shown by Examples III and IV where pure ADN was added to the cooled cycle.

The following Examples are presented to illustrate but not to restrict the present invention, parts and percentages are by weight unless otherwise specified.

In the following Examples and Comparatives the starting material was a fluid product from the hydrocyanation of 3- and/or 4-pentenenitriles, using tetrakis (tri-m&p-tolylphosphite) nickel (0) catalyst [NiL4] with excess TTP using TPB as a promoter. It had the following approximate analysis.

| Component | Amount (% by weight) |
|---|---|
| NiL4 | 0.6 (as Ni°) |
| TTP | 30 |
| Mononitriles* | 14 |
| Dinitriles** | 55 |
| TPB | 0.4 |
| Degradation Products | <1 |

*Principally 3-, 4-pentenenitriles
**Principally adiponitrile with lesser amounts of 2-methylglutaronitrile and ethylsuccinonitrile One volume of this fluid product was exhaustively extracted with 1.5 volumes of cyclohexane at the indicated temperature according to the process described in U.S. pat. No. 3,773,809. The resulting phases were separated and the cyclohexane phase was treated as described.

EXAMPLE I (E-1)

The extraction was conducted at 59° C. and the cyclohexane phase was cooled to about 23° C. whereupon a second heavier phase formed. The heavier phase was removed following which the lighter cyclohexane phase was placed in a rotary evaporator under a nitrogen atmosphere. The evaporator was heated in a water bath at 82° C. while applying vacuum generated by a water aspirator until essentially all of the cyclohexane was removed. The resulting concentrate was analyzed and the results are reported in the Table.

Approximately 130 grams of the above concentrate along with 20 grams of mixed 3-,4-pentenenitriles (approximately 97% 3-pentenenitrile and 3% 4-pentenenitrile), 0.022 ml of phosphorus trichloride and 6 grams of nickel powder (average particle size 3–7 microns, surface area 0.32–0.44 m²/gm produced by the thermal decomposition of nickel tetracarbonyl) was charged to a 250 ml flat-bottom flask fitted with a thermometer and magnetic stirrer.

The contents of the flask were analyzed for soluble nickel (less nickel powder). The results are reported in the Table. The contents of the flask were heated to 90° C. and held at that temperature for five hours with stirring following which the contents of the flask were cooled and again analyzed for soluble nickel (less unreacted nickel powder). The results of the analysis and the calculated increase in soluble nickel are reported in the Table.

COMPARATIVE I (C-1)

Example I was repeated except that the initial extraction was conducted at about 57° C. and no additional phases were separated prior to workup. The results are reported in the Table.

EXAMPLE II (E-2)

Example I was repeated except that the initial extraction was conducted at 59°-60° C. The results are reported in the Table.

COMPARATIVE II (C-2)

Comparative I was repeated except that the initial extraction was conducted at 59° C. The results are reported in the Table.

EXAMPLE III (E-3)

Example I was repeated except that the initial extraction was conducted at 60° C., the evaporation was conducted at 110° C. and 70.06 grams of concentrate, 4.0 grams of nickel powder, 0.011 ml of phosphorus trichloride and 4.94 grams of adiponitrile were charged to the reaction flask (at this point the contents of the flask analyzed 1.26% nickel (0), 68.6% tritolylphosphite, 6.6% monoitriles and 10.3% dinitriles). The results are reported in the Table.

COMPARATIVE III (C-3)

Example III was repeated except that no phases were separated prior to workup, 75.0 grams were charged to the reaction flask and no adiponitrile was added. The results are reported in the Table.

EXAMPLE IV (E-4)

Example III was repeated except that 68.72 grams of concentrate and 6.28 grams of adiponitrile were charged to the reaction flask. The contents of the flask at this point analyzed 1.67% nickel (0), 68.0% tritolylphosphite, 5.4% monoitriles and 11.9% dinitriles. The results are given in the Table.

COMPARATIVE IV (C-4)

Example IV was repeated except that no phases were separated prior to workup, 75.0 grams of concentrate were charged to the reaction flask and no adiponitrile was added.

TABLE

| Comparatives (C) Examples (E) | CONCENTRATE (WT. %) | | | | CATALYST PRODUCT Ni(o) (WT. %) | | |
| --- | --- | --- | --- | --- | --- | --- | --- |
| | Ni(o) | TTP | PN | DN | Initial | Final | Increase |
| E-1 | 0.97 | 79.9 | 7.1 | 5.0 | 0.84[1] | 1.40 | 0.56 |
| C-1 | 0.96 | 79.6 | 5.6 | 6.7 | 0.85[1] | 1.16 | 0.31 |
| E-2 | 0.94 | 75.9 | 10.5 | 5.2 | 0.79[1] | 1.39 | 0.60 |
| C-2 | 0.90 | 73.6 | 9.5 | 8.3 | 0.77[1] | 1.27 | 0.50 |
| E-3 | 1.31 | 73.4 | 7.1 | 4.0 | 1.26[2] | 1.88 | 0.62 |
| C-3 | 1.25 | 71.4 | 7.9 | 10.6 | 1.22 | 1.37 | 0.15 |
| E-4 | 1.75 | 74.2 | 5.9 | 3.9 | 1.67[2] | 2.24 | 0.57 |
| C-4 | 1.67 | 68.7 | 6.8 | 12.3 | 1.57[3] | 1.66 | 0.09 |

[1] As a result of dilution with pentenenitrile
[2] As a result of dilution with adiponitrile
[3] Analytical variance

I claim:

1. In a process for the production of dinitriles by the addition of hydrogen cyanide to pentenenitriles in the presence of a zero-valent nickel-organophosphorus ligand containing catalyst promoted with an arylborane wherein the product fluid from said addition is contacted with a paraffin or cycloparaffin at a temperature of at least about 60° C. to form a primary light hydrocarbon extract phase containing catalyst values and a heavy dinitrile phase which phases are separated and wherein said catalyst is initially prepared by reacting elemental nickel with an organophosphorus compound, the improvement which comprises cooling said primary light extract phase sufficiently to form a secondary light phase and a secondary heavy phase, separating the secondary phases, removing substantially all of said hydrocarbon from the secondary light phase, and returning at least a portion of the residue thus obtained from the secondary light phase to the initial catalyst preparation to react with said elemental nickel.

2. The process of claim 1 wherein said light phase extract is cooled to less than about 45° C.

3. The process of claim 1 wherein said light phase extract is cooled to a temperature in the range 20°–30° C.

* * * * *